(12) United States Patent
Jach

(10) Patent No.: US 6,620,302 B1
(45) Date of Patent: Sep. 16, 2003

(54) PLANAR SENSOR ELEMENT

(75) Inventor: Olaf Jach, Boeblingen (DE)

(73) Assignee: Robert Bosch GmbH, Stuttgart (DE)

( * ) Notice: Subject to any disclaimer, the term of this patent is extended or adjusted under 35 U.S.C. 154(b) by 79 days.

(21) Appl. No.: 09/868,964

(22) PCT Filed: Oct. 18, 2000

(86) PCT No.: PCT/DE00/03651
§ 371 (c)(1),
(2), (4) Date: Mar. 12, 2002

(87) PCT Pub. No.: WO01/29551
PCT Pub. Date: Apr. 26, 2001

(30) Foreign Application Priority Data

Oct. 22, 1999 (DE) .......................... 199 50 999

(51) Int. Cl.⁷ ............................................ G01N 27/407
(52) U.S. Cl. ...................................... 204/426; 204/427
(58) Field of Search ................................. 204/421–429

(56) References Cited

U.S. PATENT DOCUMENTS 5,474,665 A * 12/1995 Friese et al.
5,507,937 A * 4/1996 Renz et al.
5,653,858 A * 8/1997 Friese et al.
6,432,289 B1 * 8/2002 Uchida et al.

FOREIGN PATENT DOCUMENTS

| DE | 42 26 537 | 2/1994 |
| DE | 43 42 005 | 6/1995 |
| DE | 43 43 089 | 6/1995 |
| DE | 198 03 562 | 8/1999 |
| DE | 198 15 700 | 10/1999 |
| WO | WO 94 07 130 | 3/1994 |

* cited by examiner

Primary Examiner—T. Tung
(74) Attorney, Agent, or Firm—Kenyon & Kenyon

(57) ABSTRACT

In a planar sensor element having a gas-containing layer situated between impermeable covering layers, the gas-containing layer is enclosed by a sealing frame over its entire periphery in a plane running between the covering layers, and at least one of the covering layers has a through hole for the exchange of air (reference gas) between the gas-containing layer and the ambient environment.

5 Claims, 2 Drawing Sheets

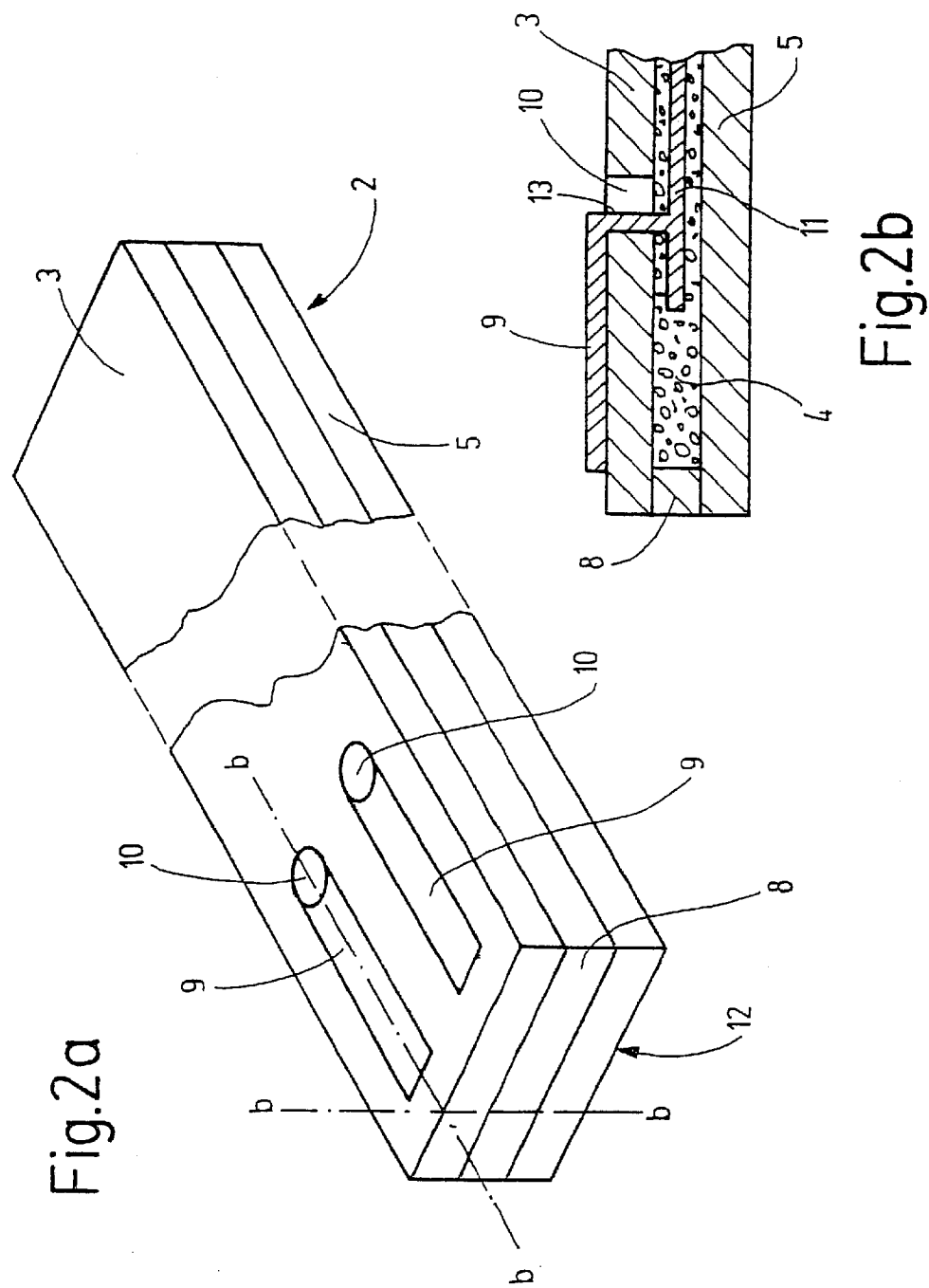

PLANAR SENSOR ELEMENT

FIELD OF THE INVENTION

The present invention relates to a planar sensor element having a gas-containing layer situated between impermeable covering layers.

BACKGROUND INFORMATION

Planar sensor elements of that kind are known and widespread as component parts of lambda sensors. Conventionally, they have impermeable covering layers made of sintered $ZrO_2$ between which an electric heating device is embedded between porous insulating layers made of aluminum oxide. The use of such insulating layers is necessary because the $ZrO_2$ used for the covering layers becomes electrically conductive at the operating temperatures which are usual for these sensor elements, which can result in leakage currents and in a falsification of the obtained measured values or even in the destruction of the sensor element and, consequently, in the failure of the lambda sensor. In contrast, aluminum has a conductivity which is smaller by several orders of magnitude.

In a lambda sensor, the air content of these porous layers can be used as pump volume for a pumped reference or as reference gas space. Also known are designs of planar sensor elements in which the reference gas space forms a hollow space within a layer. Such a layer including a hollow space which can contain the reference gas is understood here as a gas-containing layer, as well.

Usually, the gas-containing layer is brought out toward reference gas at an end face of the planar sensor element, thus forming a narrow strip at the end face via which an air exchange with the ambient environment or with the reference gas can take place.

If a sensor element is not supported absolutely gas and moisture-tight at this end face, there is a risk for moisture or exhaust components to penetrate into the gas-containing layer, resulting in the falsification of the measured values. In particular the ingress of moisture is promoted by the narrow strip shape of the passage of the gas-containing layer.

The necessity of this passage also creates difficulties in the manufacture of the sensor elements. Usually, a plurality of such sensor elements are made on a shared substrate and then separated. In this context, during the cutting of the substrate along an end face including the passage of the gas-containing layer, the edges of the substrate can easily flake off, or the notch effects arising during cutting result in imperfections at the substrate edge which, during subsequent sintering, prevent the formation of a composite having a satisfactory quality.

SUMMARY OF THE INVENTION

An improved mechanical strength of a sensor element of the type mentioned at the outset is achieved according to the present invention in that the gas-containing layer is enclosed all around by a sealing frame in a plane running between the covering layers instead of on only three sides as is the case with the conventional sensor elements, and in that at least one of the covering layers is provided with a through hole for the required exchange of air between the gas-containing layer of the sensor element and its ambient environment.

Since, during the separation of a substrate having a plurality of such sensor elements prior to sintering, only the material of the sealing frame and of the covering layers needs to be cut, i.e., usually $ZrO_2$, the wear of the cutting tools is also reduced in comparison with the case that a porous insulating layer of $Al_2O_3$ needs to be cut.

The closed sealing frame also reduces the probability of damaging the laminate structure of the sensor element when scribing and subsequently breaking the sensors along their adjacent edges during separation.

Conventional sensor elements frequently possess contact surfaces at their supported end which can be used for supplying current to a heating element or for tapping an electric signal from a measuring electrode, and which are contacted via through holes of the covering layers to conductive tracks located inside the layer structure of the sensor element. According to the present invention, these through holes are at the same time used to permit the air exchange between the gas-containing layer and the ambient environment. In this connection, the through holes have, of course, a larger cross section than the conductor which is passed through to permit the passage of gas.

To intensify the effectiveness of the overall exchange between the gas-containing layer and the ambient environment, provision can be made for the free cross-sectional area of the through holes to be larger than the free cross-sectional area of the gas-containing layer transverse to the longitudinal axis of the sensor element. This latter cross-sectional area corresponds to the gas exchange cross-sectional area of an open-edge sensor element of conventional design, as will be described in the following.

Preferably, the electric conductor which is passed through the through hole is used for supplying current to a heating element embedded in the reference-gas containing layer.

The dimensions of the through hole are no longer limited by the cross-sectional area of the gas-containing layer which is why the free diameter of the through hole can be larger than the thickness of the gas-containing layer without any problem, on one hand, to promote an efficient air exchange between the gas-containing layer and the ambient environment and, on the other hand, to prevent the through hole from exerting a strong capillary effect on liquid possibly present in its ambient environment and from drawing it into the gas-containing layer. The diameter of such a through hole should be at least 0.5, preferably approximately 1 mm.

BRIEF DESCRIPTION OF THE DRAWINGS

FIG. 2a shows a sensor element according to the present invention in a perspective view.

FIG. 2b shows the sensor element according to the present invention in a part-sectional view.

DETAILED DESCRIPTION

Figures 1A, 1B:
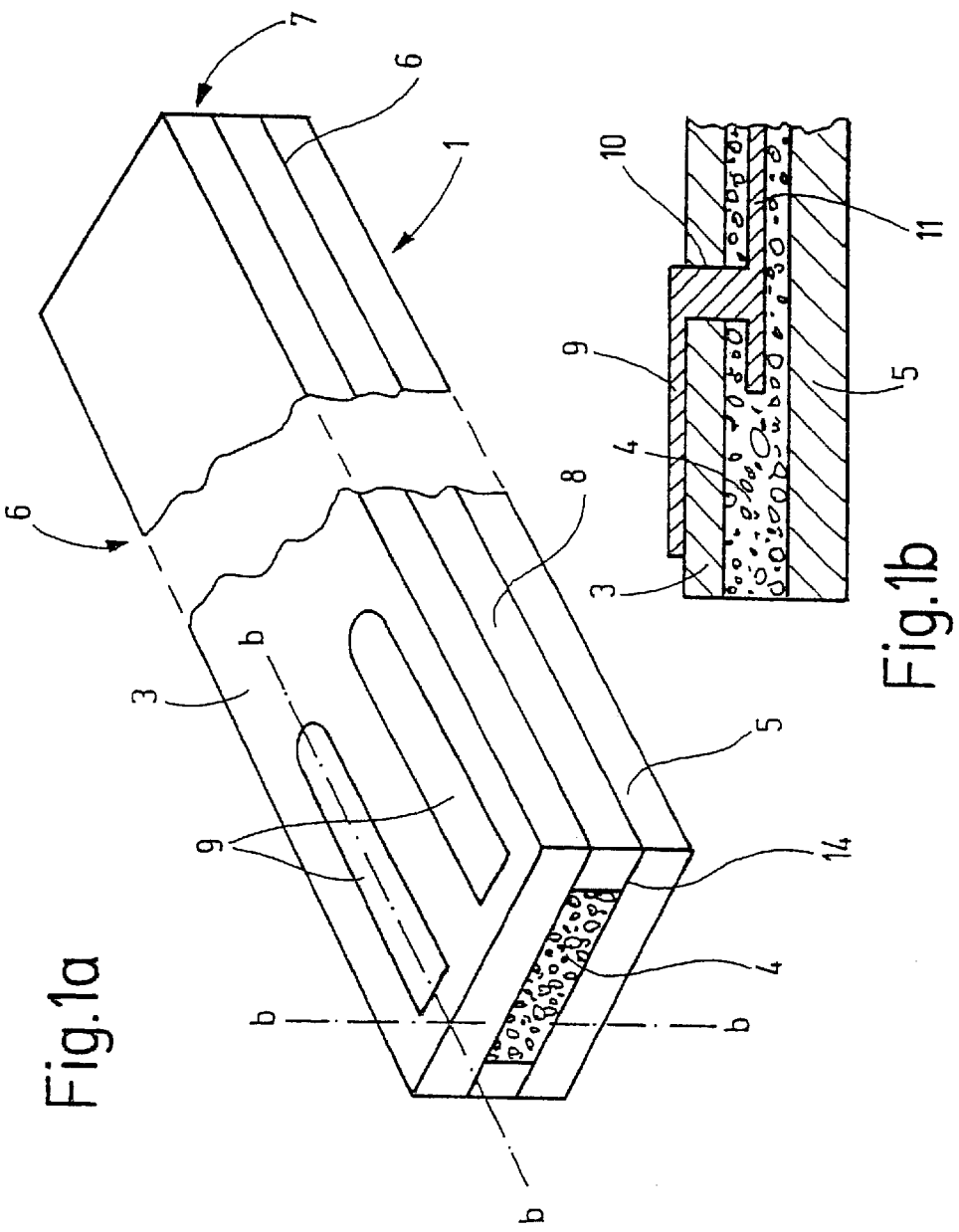
FIG. 1a shows a conventional sensor element in a perspective view.
FIG. 1b shows the conventional sensor element in a part-sectional view.

The sensor element from FIGS. 1a and 1b is composed of a plurality of sintered ceramic layers of which only those which are relevant to the present invention are shown. These are an airtight upper layer 3 made of zirconium oxide, a porous insulating layer 4 made of aluminum oxide, and an airtight lower covering layer 5, again made of zirconium oxide.

The longitudinal end of the sensor element which lies in foreground of the perspective view of FIG. 1a is intended for airtight anchoring in a socket; the opposite longitudinal end carries measuring electrodes at the surface which is located below in FIG. 1a, the measuring electrodes being relevant to the present invention only in so far as they require the interior of the sensor element to be supplied with ambient air via porous insulating layer 4 for their proper operation.

The lateral dimensions of insulating layer 4 are smaller than those of the two covering layers 3 and 5; insulating layer 4 is enclosed by a U-shaped sealing frame 8 at the two longitudinal sides 6 and at the end face 7 of sensor element 1 which faces away from the viewer, the sealing frame being sintered from zirconium oxide such as the two covering layers 3,5.

When separating jointly laminated sensor elements by cutting and breaking along longitudinal sides 6, strong shearing forces act at boundary surfaces 14 between covering layers 3,5 and sealing frame 8, the shearing forces being capable of damaging the sensor elements.

FIG. 1b depicts a section through the sensor element along the plane defined by the lines which are denoted by b in FIG. 1a. On the outer surface of upper covering layer 3, two metallic contact strips 9 are applied which serve for supplying current to a resistive heating element which is embedded in insulating layer 4 in the vicinity of end face 7. Two through holes 10 in upper covering layer 3 are filled with metal to connect the contact strips in each case with a conductive track 11 embedded in insulating layer 4 for supplying current to the heating element.

DETAILED DESCRIPTION

The sensor element 2 from FIGS. 2a and 2b according to the present invention, like that described above, has two impermeable covering layers 3,5 made of zirconium oxide as well as a porous insulating layer 4 made of aluminum oxide. However, insulating layer 4 is not visible in the in the perspective view of FIG. 2a because it is enclosed on all four sides by a surrounding sealing frame 8 made of zirconium oxide. As the section along lines b from FIG. 2a shown in of FIG. 2b, in particular the front-side end 12 of sensor element 2 facing the viewer is closed airtight by sealing frame 8. Through holes 10 are open at the surface of covering layer 3; they are filled only over a part of their cross-sectional area by a metallic connection 13 between contact strips 9 at the surface of covering layer 3 and conductor tracks 11 inside insulating layer 4. Metallic connection 13 can extend, in particular in a ring-shaped manner along the walls of the through holes. The free cross-sectional area of through holes 10 is available for the air exchange between insulating layer 4 and the ambient environment of the sensor element. The path between the measuring electrodes and the through holes which is shortened in comparison with the sensor element of FIG. 1, is an aspect which promotes the effective air exchange between the insulating layer and the ambient environment. A second aspect is the large effective cross-sectional area which can be made available at the through holes for the air exchange by selecting the diameters of through holes 10 to be large. When working with a typical layer thickness of insulating layer 4 of approximately 50 μm, a diameter of through holes 10 of 1 mm is already sufficient.

When jointly laminated sensor elements are broken apart and cut along longitudinal sides 6, arising shearing forces are distributed between the covering layers and the sealing frame over the entire width of end face 12. Therefore, the risk of damage is markedly smaller then in the case of the sensor element according to FIGS. 1a and 1b.

Moreover, a continuous laminate composite is guaranteed, as well. In fact, during sintering, shearing forces additionally arise because of sintering distortion between layers of different composition. Since in the sensor element described here, the entire outer surface is composed of the same material, no considerable shearing forces arise at its surface. Therefore, the formation of cracks at the surface of the sensor element is to be feared considerably less in the case of this sensor element than in the case of the sensor element described with reference to FIGS. 1a and b, in which insulating layer 4 of aluminum oxide comes to the surface.

What is claimed is:
1. A planar sensor element, comprising:
   a plurality of impermeable covering layers;
   a sealing frame;
   a gas-containing layer enclosed by the sealing frame over an entire periphery thereof in a plane running between the plurality of impermeable covering layers, the gas-containing layer being situated between the plurality of impermeable covering layers;
   at least one of the plurality of impermeable covering layers includes at least La one through hole for an exchange of air between the gas-containing layer and an ambient environment;
   and an electric conductor running through the at least one through hole, wherein a diameter of the conductor is less than a diameter of the at least one through hole.
2. The sensor element according to claim 1, wherein:
   the electric conductor supplies a current to a heating element embedded in the gas-containing layer or taps an electric signal from a measuring electrode of the sensor element.
3. The sensor element according to claim 1, wherein:
   the diameter of the at least one through hole is larger than a thickness of the gas-containing layer.
4. The sensor element according to claim 1, wherein:
   a cross-sectional area of the at least one through hole is larger than a cross-sectional area of the gas-containing layer transverse to a longitudinal axis of the sensor element.
5. The sensor element according to claim 1, wherein:
   the diameter of the at least one through hole is at least 0.5 mm.

* * * * *

UNITED STATES PATENT AND TRADEMARK OFFICE
CERTIFICATE OF CORRECTION

PATENT NO. : 6,620,302 B1
DATED : September 16, 2003
INVENTOR(S) : Olaf Jach

It is certified that error appears in the above-identified patent and that said Letters Patent is hereby corrected as shown below:

<u>Column 3,</u>
Line 27, delete "DETAILED DESCRIPTION"

<u>Column 4,</u>
Line 32, delete "La"

Signed and Sealed this

Twenty-seventh Day of July, 2004

JON W. DUDAS
*Acting Director of the United States Patent and Trademark Office*